United States Patent
Canetta et al.

(10) Patent No.: US 6,414,014 B1
(45) Date of Patent: *Jul. 2, 2002

(54) METHOD FOR ADMINISTRATION OF TAXOL

(75) Inventors: Renzo Mauro Canetta, Madison, CT (US); Elizabeth Eisenhauer, Kingston (CA); Marcel Rozencweig, Brandford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/499,373

(22) Filed: Feb. 7, 2000

Related U.S. Application Data

(60) Continuation of application No. 08/850,237, filed on May 2, 1997, now abandoned, which is a continuation of application No. 08/715,914, filed on Sep. 19, 1996, now Pat. No. 5,670,537, which is a continuation of application No. 08/544,594, filed on Oct. 18, 1995, now Pat. No. 5,641,803, which is a continuation of application No. 08/109,331, filed on Jun. 24, 1993, now abandoned, which is a division of application No. 07/923,628, filed on Aug. 3, 1992, now abandoned.

(51) Int. Cl.[7] ............................................ A61K 31/335

(52) U.S. Cl. ...................................... 514/449
(58) Field of Search ......................... 514/449

(56) References Cited

PUBLICATIONS

Kris et al., Cancer Treatment Reports, vol. 70, No. 5, pp 605–607 May 1986.*
Opinion Civil Action 97–6050 Mar. 1, 2000 Opinion/Order Denying Bristol–Myers Squibb's motion for summary judgment to dismiss defendant's best mode defense under 35 U.S.C. § 112.
Opinion Civil Action 97–6050 Mar. 2, 2000 Opinion/Order Denying Bristol–Myers Squibb motion for summary judgment of invalidity on the ground of obviousness, 35 U.S.C. § 103.
Opinion Civil Action 97–6050 Mar. 2, 2000 Opinion/Order Denying motion for summary judgment of noninfringement.
Opinion Civil Action 97–6050 Mar. 17, 2000 Denying summary judgment of unenforceability due to inequitable conduct.
Opinion Civil Action 97–6050 Apr. 7, 2000 Granting Bristol–Myers Squibb's request for entry of final judgment under Fed. R. Civ. P. 54(b).
W.W. ten Bokkel Huinink "Taxol," ECC Newsletter: (July 28–29, 1992).
Holmes et al., "Phase II Trial of Taxol, an Active Drug in the Treatment of Metastatic Breast Cancer", Journal of the National Cancer Institute 83:1797–1805 No. 24 (Dec. 1991).

W.W. ten Bokkel Huinink "Taxol The First Available of Taxanes, a New Class of Anticancer Drugs", *The Netherlands Cancer Institute*, Amsterdam, the Netherlands (Abstract 244) The Annales of Oncology, 3:120 (Mar. 1992).
Lipton et al., "Taxol Produces a Predominantly Sensory Neuropathy", *Neurology* (1986) 20:132.
Sewa S. Legha, MD et al., "A Phase II Trial of Taxol in Metastatic Melanoma," No. 11, pp. 2478–1481 (Jun. 1990).
Wiernik et al., "Taxol (T) Phase I and Pharmacokinetic Study", *Proceedings of ASCO*, (1986) vol 5 (Abstract 125).
J. Koeller et al., "A Phase I Study of Taxol Given as a 6 Hour Infusion Every 21 Days", *NCI–EORTC Symposium* (1989) Amsterdam (Abstract 412).
S. Lagha et al., "A Phase I Study of Taxol (NSC 125973)", *Proceedings of AACR*, (1985) vol. 26 (Abstract 684).
Rowinsky et al., "Phase I and Pharmacodynamic Study of Taxol in Refractory Acute Leukemias", *Cancer Research* (1989) 49:4640–4647.
Markman et al., "Phase 1 Study of Taxol Administered by the Intraperitoneal (IP) Route: A GOG Trial", *Proceedings of ASCO*, (1991) vol. 10 (Abstract 601).
"Taxol IND 22850 NSC 125973", a clinical brochure, National Cancer Institute, Bethesda MD (1991).
Einzig et al., "Phase II Study of Taxol (T) in patients (Pts) with Advanced Ovarian Cancer", *Proceedings of the American Association for Cancer Research* (1990) vol. 31 (Abstract 1114).
Holmes et al., "Phase II Trial of Taxol, an Active Drug in the Treatment of Metastatic Breast Cancer", *Journal of the National Cancer Institute* 83:1797–1805 No. 24 (Dec. 1991).
Einzig et al., "Phase II Trial of Taxol in Patients (Pts) with Renal Cell Carcinoma" *Proceedings of AACR* (1988) vol. 29 (Abstract) 884).
National Cancer Institute: Clinical Brochure Taxol (NSC 125973). Bethesda Maryland Division of Cancer Treatment, NCI Sep. 1983, pp. 6–12.

(List continued on next page.)

*Primary Examiner*—Jerome D. Goldberg
(74) *Attorney, Agent, or Firm*—Timothy J. Babcock

(57) ABSTRACT

Taxol dosages of about 135 mg/m$^2$ or greater are administered via infusions of less than 6 hours duration; the method makes it possible to provide taxol infusions on an out-patient basis to patients who do not otherwise require hospitalization. In a preferred embodiment, about 135 mg/m$^2$ of taxol in a cremaphor emulsion is infused over a 3 hour duration, following patient pretreatment with steroids, antihistamines, and H$_2$-receptor antagonists sufficient to prevent fatal anaphylactic-like reactions, and preferably sufficient to reduce the occurrence of severe anaphylactic-like reactions in greater than 90% of patients treated. In an alternative embodiment, between 135 mg/m$^2$ and about 175 mg/m$^2$ of taxol is provided in a 3-hour infusion, following pretreatment to minimize hypersensitivity responses. A method for rechallenging patients with taxol after episodes of acute hypersensitivity reactions is also disclosed, thus enabling patients to continue taxol therapy who would otherwise be deprived of treatment.

11 Claims, No Drawings

OTHER PUBLICATIONS

Rowinsky et al., "Sequences of Taxol & Cisplatin: Phase I/Pharmacologic Study", *Proceedings of ASCO* (1990) vol. 9 (Abstract 290).

Einzig et al., "Phase II Pilot Study of Taxol in Patients (Pts) with Malignant Melanoma (MM)" *Proceedings of ASCO* (1988) vol. 7 (Abstract 963).

Longnecker et al., "High–Performance Liquid Chromatographic Assay for Taxol in Human Plasma and Urine and Pharmacokinetics in a Phase I Trial", *Cancer Treatment Reports* (1987) 71:53–59 No. 1.

Lipton et al., "Taxol Produces a Predominantly Sensory Neuropathy", *Neurology* (1989) 39:368–373.

*Gynaecological Cancer Newsletter*, Gynaecological Oncology Group of Victoria (1990) No. 6 pp. 1–21.

G. Sarosy et al., "Taxol Dose Intensification (D.I.) in Patients with Recurrent Ovarian Cancer", *Proceedings of ASCO* (1992) vol. 11 (Abstract 716).

A. Seidman et al., "Activity of Taxol with Recombinant Granulocyte Colony Stimulating Factor (FCSF) as First Chemotherapy (C) of Patients (PTS) with Metastatic Breast Cancer (MBC)", *Proceedings of ASCO* (1992) vol. 11 (Abstract 64).

Murphy, "A Phase II Study of Taxol (NSC 125973) in Patients (PTS) with Non–Small Cell Lung Cancer (NSCLC)", *Proceedings of ASCO* (1992) vol. 11 (Abstract 985).

Chang et al., "Phase II Study of Taxol in Patients with Stage IV Non–Small Cell Lung Cancer (NSCLC); The Eastern Cooperative Oncology Group (ECOG) Results", *Proceedings of ASCO* (1992) vol. 11 (Abstract 981).

Roth et al. "Taxol (NSC 125973) in Advanced Hormone–Refractory Prostate Cancer: an ECOG Phase II Trial", *Proceedings of ASCO* (1992) vol. 11 (Abstract 598).

Spriggs et al, "Taxol Administered as a 120 Hour Infusion", *Investigational New Drugs* (1992) 10:275–278.

Editorial: "Taxol: Twenty Years Later, the Story Unfolds", Rowinsky et al., *Journal of National Cancer Institute* (1992) pp. 1178–1181.

W.W. ten Bokkel Huinink "Taxol The First Available of Taxanes, a New Class of Anticancer Drugs", *The Netherlands Cancer Institute*, Amsterdam, the Netherlands (Abstract 244) The Annales of Oncology, 3:120 (Mar. 1992).

Chabner, "Taxol", *Principles & Practice of Oncology* (1991) 5:1–10 No. 9.

Longnecker et al., "Phase I and Pharmacokinetic Study of Taxol in Patients with Advanced Cancer", *Proceedings of ASCO*, (Mar., 1985) vol. 4 (Abstract C–119).

Tutsch, K.D. et al., "Phase I Clinical Trial with Pharmacokinetic Analysis of Taxol (NSC 125973) Given on a Daily x5 Schedule" *Proceedings from the American Society of Clinical Oncology*, (Mar. 1985), vol. 4, p. 40, Abstract No. C–151.

J. Brown et al. *Canadian Oncology Nursing J.* (Feb. 1992), pp. 47–50.

T. Peretz et al., *Eur. J. Cancer*, vol. 31A, Supp. 5, p. 575 (1995).

Mcguire et al., "Taxol: A Unique Antineoplastic Agent with Significant Activity Against Advanced Ovarian Epithelial Neoplasms," *Ann. Int. Med.*, 111, 273–279 (1989).

Brown et al, "A Phase I Trial of Taxol Given by a 6–Hour Intravenous Infusion,", *Journal of Clinical Oncology*, vol. 9, No. 7, pp. 1261–1267 (Jul. 1991).

Kris et al., "Phase I Trial of Taxol Given as a 3–Hour Infusion Every 21 Days," *Cancer Treatment Reports*, vol. 70, No. 5, pp. 605–607 (May 1985).

Einzig et al., "Phase II Trial of Taxol in Patients with Metastatic Renal Cell Carcinoma," *Cancer Investigation* 9(2) 133–136 (1991).

A.B. Miller et al., "Reporting Results of Cancer Treatment," *Cancer*, vol. 47, pp. 207–214 (1981).

Koeller et al., "A Phase I/Pharmacokinetic Study of Taxol Given by a Prolonged Infusion Without Premedication," *Proceedings of ASCO* , vol. 8, p. 82 (Mar. 1989).

Wiernik et al., "Phase I Clinical and Parmacokinetic Study of Taxol," *Cancer Research*, 47, 2486–2393 (May 1, 1987).

Legha et al., "Phase I Study of Taxol Using a 5–Day Intermittent Schedule," *Journal of Clinical Oncology*, vol. 4, No. 5, pp. 762–766 (May 1986).

Rowinsky et al., "Phase I Study of Taxol in Refractory Adult Acute Leukemia," *Proceedings of AACR* vol. 29, p. 215 (Mar. 1985).

Gremm et al., "Phase I Study of Taxol Administered as a Short IV Infusion Daily for 5 Days," *Cancer Treatment Reports* vol. 71, No. 12 (Dec. 1987).

Donehower et al., "Phase I Trial of Taxol in Patients with Advanced Cancer," *Cancer Treatment Reports* vol. 71, No. 12 (Dec. 1987).

Holmes et al., "Phase II Study of Taxol in Patients (PT) with Metastatic Breast Cancer (MBC)," *Proceedings of the American Society of Clinical Oncology* vol. 10, p. 60 (Mar. 1991).

Suffness, "Development of Antitumor Natural Products at the National Cancer Institute," *Gann Monograph on Cancer Research*, 36, pp. 21–44 (1989).

Weiss et al., "Hypersensitivity Reactions from Taxol," *Journal of Clinical Oncology* vol. 8, No. 7, pp. 1263–1268 (Jul. 1990).

Sorosy et al., "Phase I Stud of Taxol and Granulocyte Colony–Stimulating Factor in Patients with Refractory Ovarian Cancer," *Journal of Clinical Oncology*, vol. 10, No. 7, pp. 1165–1170 (Jul. 1992).

Ohnuma et al., "Phase I Study of Taxol in a 24–Hour Infusion Schedule," *Proceedings of AACR*, vol. 26, p. 167 (Mar. 1985).

Wiernik et al., "Phase I Trial of Taxol Given as a 24–Hour Infusion Every 21 Days: Response Observed in Metastatic Melanoma," *Journal of Clinical Oncology*, vol. 5, No. 8, pp. 1232–1239 (Aug. 1987).

Brown et al., "Taxol: Women with Ovarian Cancer Participate in a New Clinical Trial," *Canadian Oncology Nursing Journal* 47–50 (Feb. 2, 1992).

Longnecker et al., "Phase I and Pharmacokinetic Stud of Taxol in Patients with Advanced Cancer," *Proceedings of the American Society of Clinical Oncology* vol. 4, p. 32 (Mar. 1985).

T. Thigpen et al., "Phase II Trial of Taxol as Second–Line Therapy for Ovarian Carcinoma: A Gynecologic Oncology Group Study," *Proceedings of ASCO* vol. 9, p. 156 (Mar. 1990).

Sewa S. Legha, MD et al., "A Phase II Trial of Taxol in Metastatic Melanoma," No. 11, pp. 2478–1481 (Nov. 8, 1989).

Eric K. Rowinsky et al., "Taxol: A Novel Investigational Antimicrotubule Agent," vol. 82, No. 15, pp. 1247–1259 (Aug. 1, 1990).

Avi I. Einzig et al., "A Phase II Study of Taxol in Patients with Malignant Melanoma," *Investigational New Drugs 9*, pp. 59–64 (1991).

O'Connell, Kris et al, "Phase I Trial of Taxol Given as a Three Hour Infusion Every Three weeks", *Seventy–Six Annual Meeting of the Amer. Assoc. for Cancer Research Proceedings*, May 22–25, 1985, vol. 26, Abstract 671 (Mar. 1985).

Rowinsky & McGuire, "Taxol", Editorials, *The Lancet*, vol. 339, No. 8807, pp. 1447–1452 (Jun. 13, 1992).

Rowinsky & McGuire, "Taxol: Present Status and Future Prospects", *Contemporary Oncology*, pp. 29–36 (Mar. 1992).

Eisenhauer et al., "European–Canadian Randomized Trial of Paclitaxel in Relapsed Ovarian Cancer: High–Dose Versus Low–Dose and Long Versus Short Infusion", *Journal of Clinical Oncology*, vol. 12, No. 12, pp. 2654–2666 (Dec. 1994).

Rowinsky et al., "Taxol: The First of the Taxanes, an Important New Class of Antitumor Agents", Seminars in Oncology, vol. 19, No. 6, pp. 646–662 (Dec. 1992).

booklet: Workshop on Taxol and Taxus: Current and Future Perspectives; Sponsored by: Developmental Therapeutics Program, Division of Cancer Treatment, National Cancer Institute; Jun. 26, 1990.

E.L. Trimble et al., "Paclitaxel for Platinum–Refractory Ovarian Cancer: Results From the First 1,000 Patients Registered to National Cancer Institute Treatment Referral Center 9103", *Journal of Clinical Oncology*, vol. 11, No. 12, pp. 2405–2410 (Dec. 1993).

Notices: Department of Health and Human Services, National Institutes of Health: 54 FR 31733; Aug. 1, 1989.

Greenberger, et al., J. Allergy Clin, Immunol., vol. 87, No. 4. pp. 867–872 (1991).

Philibin, et al., Anesthesiology, vol. 55, pp. 292–296 (1981).

Weiss, Seminars in Oncology, vol. 9, No. 1, pp. 5–13 (1982).

Kaliner, et al., J. Allergy Clin. Immunol., vol. 69, No. 3, pp. 283–289 (1982).

Letter from Susan Arbuck to Nicole Onetto dated Jan. 30, 1992.

Opinion 00–1304, Court of Appeals for the Federal Circuit, dated Apr. 20, 2001.

Opinion 00–1304, Court of Appeals for the Appeals for the Federal Circuit, dated Apr. 20, 2001.

\* cited by examiner

METHOD FOR ADMINISTRATION OF TAXOL

This application is a continuation of application Ser. No. 08/850,237, filed May 2, 1997, now abandoned which is a continuation of Ser. No. 08/715,914, filed Sep. 19, 1996; now U.S. Pat. No. 5,670,537, which is a continuation of Ser. No. 08/544,594, filed Oct. 18, 1995now U.S. Pat. No. 5,641,803, which is a continuation of Ser. No. 08/109,331, filed Jun. 24, 1993, now abandoned, which is a divisional of Ser. No. 07/923,628, filed Aug. 3, 1992, now abandoned.

FIELD OF THE INVENTION

The present invention is directed to methods of cancer treatment with taxol, and more particularly is directed to improvements in the administration of taxol in the treatment of cancer.

BACKGROUND OF THE INVENTION

Taxol is a naturally occurring compound which has shown great promise as an anti-cancer drug. For example, taxol has been found to be an active agent against drug-refractory ovarian cancer by McGuire et al. See "Taxol: A Unique Anti-Neoplastic Agent With Significant Activity Against Advanced Ovarian Epithelial Neoplasms," *Ann. Int. Med.*, 111, 273–279 (1989). All patents, scientific articles, and other documents mentioned herein are incorporated by reference as if reproduced in full below.

Unfortunately, taxol has extremely low solubility in water, which makes it difficult to provide a suitable dosage form. In fact, in Phase I clinical trials, severe allergic reactions were caused by the emulsifiers administered in conjunction with taxol to compensate for taxol's low water solubility; at least one patient's death was caused by an allergic reaction induced by the emulsifiers. Dose limiting toxicities include neutropenia, peripheral neuropathy, and hypersensitivity reactions.

Brown et al, in "A Phase I Trial of Taxol Given By A 6-Hour Intravenous Infusion" *J of Clin Oncol*, Vol. 9, No. 7, pp. 1261–1267 (July, 1991) report on a Phase I Trial in which taxol was provided as a 6-hour IV infusion every 21 days without premedication. 31 patients received 64 assessable courses of taxol. One patient had a severe (or acute) hypersensitivity reaction, which required discontinuation of the infusion and immediate treatment to save the patients life. Another patient experienced a hypersensitivity reaction, but it was not so sever as to require discontinuing the infusion. Myelosuppression was dose-limiting, with 2 fatalities due to sepsis. Non-hematologic toxicity was of Grade 1 and 2, except for one patient with Grade 3 mucositis and 2 patients with Grade 3 neuropathy. The neuropathy consisted of reversible painful paresthesias, requiring discontinuation of taxol in two patients. Four partial responses were seen (3 in patients with non-small-cell lung cancer, and one in a patient with adenocarcinoma of unknown primary). The maximum tolerated dose reported was 275 mg/m$^2$, and the recommended Phase II starting dose was 225 mg/m$_2$. The incidence of hypersensitivity reaction was reported to be schedule-dependent, with 6 to 24-hour infusions of drug having a 0% to 8% incidence of hypersensitivity reactions. It was also reported that hypersensitivity reactions persist with or without premedication despite prolongation of infusion times. Since these Phase I studies were conducted on terminally ill patients suffering from a variety of cancers, the efficacy of the taxol treatments could not be determined.

In a study by Kris et al., taxol formulated with Cremaphor EL in dehydrated alcohol was given as a 3-hour IV infusion every 21 days, with the administered dosage ranging from 15 to 230 mg/m$^2$ in nine escalation steps. Kris et al. concluded that "with the severity and unpredictability of the hypersensitivity reactions, further usage of taxol is not indicated with this drug formulation on this administration schedule." See *Cancer Treat. Rep.*, Vol. 70, No. 5, May 1986.

Since early trials using a bolus injection or short (1–3 hour) infusions induced anaphylactic reactions or other hypersensitivity responses, further studies were carried out in which taxol was administered only after premedication with steroids (such as dexamethasone), antihistamines (such as diphenhydramine), and H$_2$-antagonists (such as cimetidine or ranitidine), and the infusion time was extended to 24 hours in an attempt to eliminate the most serious allergic reactions. Various Phase I and Phase II study results have been published utilizing 24-hour infusions of taxol with maximum total dosages of 250 mg/m$^2$, generally with the course being repeated every 3 weeks. Patients were pretreated with dexamethasone, diphenhydramine, and cimetidine to offset allergic reactions. See Einzig, et al., "Phase II Trial of Taxol in Patients with Metastatic Renal Cell Carcinoma," *Cancer Investigation*, 9(2) 133–136 (1991), and A. B. Miller et al., "Reporting Results of Cancer Treatment," *Cancer*, Vol 47, 207–214 (1981).

Koeller et al, in "A Phase I Pharmacokinetic Study of Taxol Given By a Prolonged Infusion Without Premedication," *Proceedings of ASCO*, Vol. 8 (March, 1989), recommends routine premedication in order to avoid the significant number of allergic reactions believed to be caused by the cremaphor (polyethoxylated castor oil) vehicle used for taxol infusions. Patients received dosages ranging from 175 mg/m$^2$ to 275 mg/m$^2$.

Wiernik et al, in "Phase I Clinical and Pharmacokinetic Study of Taxol," *Cancer Research*, 47, 2486–2495 (May 1, 1987), also report the administration of taxol in a cremaphor vehicle by IV infusion over a 6-hour period in a Phase I study. Grade 3–4 hypersensitivity reactions incurred in 4 of 13 courses. The starting dose for the study was 15 mg/m$^2$ (one-third of the lowest toxic dose in dogs). Doses were escalated, and a minimum of 3 patients were treated at each dose level until toxicity was identified, and then 4–6 patients were treated at each subsequent level. The study concluded that neurotoxicity and leucopenia were dose-limiting, and the recommended Phase II trial dose was 250 mg/m$^2$ with premedication.

Other exemplary studies on taxol include: Legha et al, "Phase II Trial of Taxol in Metastatic Melanoma," Vol. 65 (June 1990) pp. 2478–2481: Rowinsky et al, "Phase I and Pharmacodynamic Study of Taxol in Refractory Acute Leukemias," *Cancer Research*, 49, 4640–4647 (Aug. 15, 1989); Grem et al, "Phase I Study of Taxol Administered as a Short IV Infusion Daily for 5 Days," *Cancer Treatment Reports*, Vol. 71 No. 12, (December, 1987); Donehower et al., "Phase I Trial of Taxol in Patients With Advanced Cancer," *Cancer Treatment Reports*, Vol. 71, No. 12, (December, 1987); Holmes et al, "Phase II Study of Taxol in Patients (PT) with Metastatic Breast Cancer (MBC)," *Proceedings of the American Society of Clinical Oncology*, Vol. 10, (March, 1991), pp. 60. See also Suffness, "Development of Antitumor Natural Products at the National Cancer Institute," *Gann Monograph or Cancer Research*, 31 (1989) pp. 21–44 (which recommends that taxol only be given as a 24-hour infusion).

Weiss et al., in "Hypersensitivity Reactions from Taxol," *Journal of Clinical Oncology*, Vol. 8, No. 7 (July 1990) pp.

1263–1268, reported that it was difficult to determine a reliable overall incidence of hypersensitivity reactions, HSRs, because of the wide variations in taxol doses and schedules used, and the unknown degree of influence that changing the infusion schedule and using premedication has on HSR incidents. For example, of five patients who received taxol in a 3-hour infusion at greater than 190 mg/m$^2$ with no premedication, three had reactions, while only one out of 30 patients administered even higher doses over a 6-hour infusion with no premedication had a reaction. Therefore, this suggests that prolonging the infusion to beyond 6 hours is sufficient to reduce HSR incidents. Nevertheless, Weiss et al. found that patients receiving 250 mg/m$^2$ of taxol administered via a 24-hour infusion still had definite HSRs. Thus, while prolonging drug infusion to 6 or 24-hours may reduce the risk for an acute reaction, this conclusion can not be confirmed, since 78% of the HSR reactions occurred within ten minutes of initiating the taxol infusion, which indicates that the length of time planned for the total infusion would have no bearing. Further, concentration of taxol in the infusion may also not make a difference since substantial numbers of patients had reactions to various small taxol dosages. Finally, not only is the mechanism of taxol HSR unknown, it is also not clear whether taxol itself is inducing HSRs, or if the HSRs are due to the excipient (Chemophor EL; Badische Anilin und Soda Fabrik AG [BASF], Ludwigshafen, Federal Republic of Germany). Despite the uncertainty as to whether or not premedication had any influence on reducing the severity or number of HSRs, prophalactic therapy was recommended, since there is no known danger from its use.

The conflicting recommendations in the prior art concerning whether premedication should be used to avoid hypersensitivity reactions when using prolonged infusion durations, and the lack of efficacy data for infusions done over a six hour period has led to the use of a 24-hour infusion of high doses (above 170 mg/m$^2$) of taxol in a Cremaphor EL emulsion as an accepted cancer treatment protocol.

Although it appears possible to minimize the side effects of administering taxol in an emulsion by use of a long infusion duration, the long infusion duration is inconvenient for patients, and is expensive due to the need to monitor the patients for the entire 6 to 24-hour infusion duration; Further, the long infusion duration requires that patients spend at least one night in a hospital or treatment clinic.

Thus, it is highly desirable to develop a taxol infusion protocol which would allow for recipients to be treated on an out-patient basis. Since taxol infusions are generally preceded by premedication, and require post-infusion monitoring and record keeping, it is highly desirable that the infusion duration not exceed 6 hours, yet the infusion dosage should provide the patient sufficient taxol to have an anti-neoplastic effect, while not exceeding dose-limiting toxicities. It is also desirable to minimize premedication since this increases patient discomfort and increases the expense and duration of treatment.

Even if infusion duration can not be shortened, it is also desirable to avoid the high dosages of taxol presently believed necessary to have an anti-neoplastic effect, which induce a variety of adverse side-effects, including respiratory distress, cardiovascular irregularities, flu-like symptoms, gastrointestinal distress, hematologic complications, genitourinary effects, neuropathy, alopecia, and skin rashes.

Further, due to the extremely limited supply of taxol, and the high dosage requirement for each patient, the demand for taxol greatly exceeds the supply.

Therefore, it is highly desirable to reduce taxol dosages, if possible, to both extend the supply of taxol and reduce the toxic side effects of taxol. It is also highly desirable to decrease the time required to administer taxol to patients to minimize patient discomfort and expense.

Thus, there is a need for a new method of administration of taxol which utilizes less taxol and/or requires less infusion time.

Therefore, it is a primary object of the present invention to provide a new method for administering taxol over a shorter period of time than the present 6 to 24-hour infusion protocols, while minimizing toxic effects induced by the administration of taxol.

It is another object of the present invention to provide a new method for administration of taxol which reduces the amount of taxol administered to a patient, without sacrificing the anti-neoplastic effects desired by administering taxol.

It is yet a further object of the present invention to provide a new method for administration of taxol which utilized both lower dosages of taxol and shorter infusion periods, without sacrificing the anti-neoplastic benefits of the administration of taxol.

SUMMARY OF THE INVENTION

These and other objects of the present invention are accomplished by new methods of administration of taxol. In a preferred embodiment, taxol infusions are provided over a duration of less than six hours, preferably about three hours, utilizing dosages of between about 135 mg/m$^2$ and about 275 mg/m$^2$, preferably between about 135 mg/m$^2$ and about 175 mg/m$^2$, after patients are pretreated to alleviate or minimize hypersensitivity responses. In a preferred embodiment, anti-neoplastic effects are achieved in patients suffering from cancer through administration of about 135 mg/m$^2$ administered via a 3-hour infusion following premedication to reduce or eliminate hypersensitivity responses. These results are surprising in view of the conventional understanding that a bolus injection or short (1–3 hour infusions) will induce anaphylactic reactions or other hypersensitivity responses, and that only premedication coupled with extension of the infusion time to 6–24 hours would reduce or eliminate the most serious allergic reactions.

In an alternative embodiment, 135 mg/m$^2$, taxol is administered via a 24-hour infusion following premedication. Preferably, patients are premedicated with steroids, antihistamines, and $H_2$-antagonists sufficient to at least prevent an anaphylactoid shock capable of causing patient death in greater than 95% of cancer patients treated, and avoid acute hypersensitivity reactions in greater than 90% of cancer patients treated.

To ameliorate myelosuppression associated with taxol administration, particularly associated with high dosages of taxol, granulocyte-colony stimulating factor (G-CSF) is given as a daily subcutanious injection started 24-hours after the completion of a taxol infusion. With the use of G-CSF, taxol dosages of up to 275 mg/m$^2$ can be safely administered using the methods of the present invention.

Other aspects of the present invention include a method of administering taxol to a patient suffering from cancer by monitoring certain clinical parameters, and temporarily haulting taxol administration when infusion related toxicities exceed safe limits. After the parameters return to near baseline, therapy is restarted, preferably with 72 hours. In a preferred embodiment, premedication is given intravenously prior to restarting the infusion. For patients suffering sever HSRs near the end of, or after, a taxol infusion, the HSR is treated, and the patient is rechallenged during the next course by providing premedication intravenously, followed by using a modified 24-hour infusion, in which the infusion is initiated at about one fourth the planned infusion 24-hour rate; if there are no sever HSR symptoms after about six hours, the infusion is continued at the 24-hour rate. Additional aspects include the administration of multiple courses of taxol over regular periods of time, such as at approximately 21-day intervals, or when adverse effects of a previous course or infusion substantially subside.

DETAILED DESCRIPTION OF THE INVENTION

Despite the conventional understanding that it is necessary to infuse patients over a 24-hour period with high dosages of taxol (greater than 170 mg/m$^2$) following premedication to minimize or eliminate hypersensitivity responses, while obtaining the desired anti-neoplastic effect, it has been surprisingly discovered that taxol can be safely administered to cancer patients via infusions lasting less than 6 hours at dosages of about 135 mg/m$^2$ to about 175 mg/m$^2$. In a preferred embodiment, taxol is administered via an infusion having a duration of about three hours, with a taxol dosage of about 135 mg/m$^2$ or about 175 mg/m$^2$. Of great significance is a surprising discovery that the short term infusion causes less myelosuppression, which leads to a lower incidence of infections and fever episodes (e.g., febrile neutropenia). Following the preferred infusion schedules of the present invention provides an objective response rate of greater than 10% for patients suffering from epithelial ovarian carcinoma, and preferably an objective response rate of 14% or greater for groups of at least 150 patients suffering from ovarian carcinoma.

The surprising discovery that taxol could be safely administered via a short infusion (e.g., less than six hours and preferably over about 3 hours) means that it will now be possible to administer taxol on an out-patient basis, saving patients the time and expense of yet another hospitalization while improving patient quality of life.

It has been surprisingly discovered that lower taxol dosages, such as about 135 mg/m$^2$ can be administered via infusions lasting about 3-hours to about 28-hours, and still be antineoplastically effective.

Experimental Protocol

A multi-center, randomized comparative study of taxol in patients suffering from ovarian carcinoma which had been pretreated with platinum was carried out. The high degree of success, greater than 10% of objective response, to treatment by patients suffering from drug refractory ovarian carcinoma is truly astonishing, since responses to drug refractory ovarian carcinoma are extremely uncommon. While experimental data is provided herein for the successful treatment of ovarian carcinoma with taxol using the present treatment protocol, it is to be understood that the treatment protocol can be used for the treatment of other forms of cancer with taxol, such as melanoma, renal cell carcinoma, and other cancers which are treatable with taxol. The present invention provides an improvement in the treatment of all types of cancer which can be treated with taxol, since by use of the administration protocol of the present invention, lower toxicities and/or less time is required than that associated with prior art protocols for administering antineoplastically effective amounts of taxol.

Patients with platinum pretreated recurrent ovarian cancer were randomized to a 135 or 175 mg/m$^2$ dose arm, administered as a 3-hour or 24-hour IV infusion, which was repeated every three weeks. Responses were evaluated every two cycles. All four treatment groups were matched for age, performance status, previous treatments, and time from last platinum therapy. If a patient showed a complete response, CR, taxol infusions were continued for four cycles post CR; patients showing a partial response, PR, had taxol infusions continued until relapse, or treatment was stopped after four cycles post PR stabilization. For a stable disease, taxol infusions were stopped after a maximum of 10 cycles or earlier if unacceptable toxicity was present; if disease progressed, PD, patients were taken off the study.

The study included four arms as indicated below:

| ARM | INFUSION DURATION | DOSAGE |
|---|---|---|
| A | 24 hours | 175 mg/m$^2$ |
| B | 3 hours | 175 mg/m$^2$ |
| C | 24 hours | 135 mg/m$^2$ |
| D | 3 hours | 135 mg/m$^2$ |

Patients with ovarian carcinoma included in the study had been treated with and were unresponsive to a minimum of one but no more than two platinum-containing chemotherapy regimens, and were required to have shown progression during or relapse after their last regimen of chemotherapy. Patients were treated every 21 days if allowed by toxicity. Granulocyte count and platelet count were monitored; provided granulocyte count was at least 1500 cells/cmm and platelet count was at least 100,000 cells/cmm, taxol was administered.

Administration of Taxol

Prior to initiating an infusion, a resussitation/emergency cart was placed outside the infusion room and remained there during the first hour of infusion. An emergency drug tray having all the necessary drugs, etc . . . was set up in the room in the event of an acute hypersensitivity reaction. Oxygen and suction equipment are provided at the bedside of each patient along with a 3-hour or 24-hour observation sheet (depending on the arm), and a fluid balance sheet.

Nitroglycerin tubing is required for the IV equipment because the Cremaphor EL (polyethoxylated castor oil) leaches plasticizer from regular IV tubing made of polyvinylchloride. Glass or polyolefin containers were used for storing all cremophor containing solution. All taxol-containing solutions were infused with in-line filtration using a microporous filter, preferably having a pore size not greater than 0.22 microns.

In order to minimize acute hypersensitivity reactions, patients were premedicated according to the protocol with dexamethasone or an equivalent (20 mg taken os at home, 12 hours and 6 hours prior to taxol infusion). Diphenhydramine (or equivalent antihistamine), 50 mg IV; and ranitidine (or equivalent H-2receptor blocker), 50 mg IV, were provided 30 minutes prior to the taxol infusion.

Taxol was supplied by BRISTOL-MYERS SQUIBB as a concentrated sterile solution for IV administration. Each 5 ml vial contained 6 mg/ml taxol in polyethoxylated castor oil (Cremaphor EL) 50% in dehydrated alcohol, USP 50%. While an emulsion of taxol in polyethoxylated caster oil in dehydrated alcohol is utilized as a vehicle in a preferred embodiment, it is contemplated that other pharmaceutically acceptable vehicles for taxol may be used.

Taxol was administered, after dilution in dextrose or saline solution, as a continuous infusion in two 500 ml glass bottle of 5% dextrose (D5W) or normal saline (NS) over 3 hours, or in two 500 mL glass bottles over 12 hours each for the 24-hour infusion. The first 18 mL of IV solution were infused at a fast rate (300 mL/hour) via the previously primed line to ensure that the taxol had reached the end of the IV tubing. This procedure enables the accurate accessment of the patient receiving the taxol.

A nurse remained with each patient for the first hour of each infusion. Temperature, pulse, blood pressure, and respiration were taken preinfusion, every 15 minutes for the first hour, every thirty minutes for the next 2 hours, hourly for the next 4 hours, and every other hour until the end of the infusion (for patients receiving the 24-hour infusion). Other observations were also documents, such as rash/redness of the skin, hives, vomiting, nausea, and any other symptoms including neuropathy and skin rashes.

Another aspect of the present invention is that patients suffering from hypersensitivity reactions to taxol infusions can be retreated with taxol following management of the hypersensitivity reaction. In a preferred embodiment, patients experiencing hypersensitivity reactions were taken off taxol. Hypersensitivity reactions were treated by administration of diphenhydramine (50 mg IV) with administration of epinephrine 0.35–0.5 cc s.c. every 15–20 minutes until reaction subsided or until a total of six dosages of epinephrine were given. IV fluids were administered when hypotension did not respond to epinephrine. Likewise, if wheezing did not stop in response to epinephrine, 0.35 cc of neubulized albuterol solution was administered.

To prevent recurrent or ongoing allergy manifestation, 125 mg methylprednisolone was administered via IV.

In a preferred embodiment for rechallenging with taxol patients who had experienced a hypersensitivity reaction (other than hypotension requiring pressor therapy, angioedema respiratory distress requiring bronchodilation therapy, and generalized urticaria), the following protocol was followed. All rechallenge patients received a prolonged 24-hour infusion, even if the hypersensitivity reaction occurred during a 3-hour infusion. Dosage reductions in subsequent treatment courses were mandated for all patients having (1) a granulocyte count of less than 500 cells/cmm, (2) a platelet count of less than 50,000 cells/cmm for seven days or more, (3) febrile neutropenia, (4) infection, (5) hemmorage, (6) mucositis with vesiculation and/or ulcers, or (7) vomiting appearing despite anti-emitic premedication. Taxol treatment was discontinued in patients having (1) intolerable paresthesias and/or marked motor loss (neurological toxicity of World Health Organization, WHO, grade greater than 2); (2) symptomatic bradycardia or heart block of any degree or other arrhythmias; and (3) other major organ toxicity of WHO grade greater than 2.

If less than 75% of a total taxol dose was infused prior to a hypersensitivity reaction, retreatment preferably occurs within 72 hours of cessation of taxol infusion, and the amount of taxol used for retreatment equals the originally planned taxol dose less the amount infused before the taxol infusion was stopped due to the hypersensitivity reaction. A non-limiting embodiment of a preferred rechallenge procedure follows:

A. A steroid is given. For example, 8 mg dexamethasone is given intravenously 24, 18, 12, and 6 hours prior to taxol administration.

B. An antihistamine is given 30 minutes prior to taxol, for example, 50 mg IV diphenhydramine.

C. An H2 receptor antagonist is given 30 minutes prior to taxol infusion, for example, ranitidine 50 mg IV.

D. Taxol is administered in the 24-hour infusion volume, but at one quarter the planned rate for a 24-hour IV infusion during the first 6 hours. If no reaction is noted, the rate is increased to normal infusion speed. Thus, the entire infusion time is somewhat longer than 24 hours because of the slow infusion during the first 6 hours. Thus, by way of non-limiting example, total infusion time would be approximately 28.5 hours.

E. If a hypersensitivity reaction sufficient to discontinue the taxol infusion recurs during the rechallenge procedure; the patient is taken off taxol. However, if a patient is successfully rechallenged without recurrence of a hypersensitivity reaction severe enough to require discontinuation of the infusion, the rechallenge procedure is continued.

EFFICACY AND SAFETY

In order to confirm the efficacy and safety of the taxol administration method of the present invention, patients with histologically confirmed ovarian carcinoma, who had shown progression during or relapse after platinum-containing therapy, were administered taxol according to one of the four previously described Arms. Patients ranged between 18 and 75 years in age with an Eastern Cooperative Oncology Group, ECOG, performance status of 0, 1, or 2, and had to have recovered from all toxicities of previous treatment. Further, no prior chemotherapy or radiotherapy were allowed within four weeks prior to entry into the study (patients were also not entered into the study if there had been less than six weeks since prior mitomycin, nitrosureas, or high-dose carboplatin therapy). An adequate baseline bone marrow function was required, which was defined as a granulocyte count $\geq 2,000$ cells/cmm and a platelet count $\geq 100,000$ cells/cmm. Adequate hepatic and renal functions were required with normal hepatic function defined as total billirubin $\leq 1.5$ times upper normal value and normal renal function defined as serum creatinine $\leq 1.5$ times upper normal value. Patients with abdominal adenocarcinoma, a previous history of a trial or ventricular arrhythmias, congestive heart failure, myocardial infarction within six months preceding randomization, complete bowel obtruction, a pre-existing neuropathy <WHO grade 2, active infection, prior allergic reaction to drugs containing Cremaphor, or other serious medical condition were excluded from this study.

Eligible patients were randomized according to a computerized randomization log. During therapy, hematology data (hemoglobin, white blood cell count, granulocytes and platelets) were collected, and toxicity assessments were continuously made. After each cycle, a physical history update was recorded, as well as tumor measurement, performance status (ECOG), hematology, chemistry (serum creatinine, billirubin, alkaline phosphatase, (SLOT (AST), CA125) and a toxicity assessment. A quality of life assessment was also made after each cycle, and every two months until six months after treatment stopped.

The efficacy and safety of the improved method for administration of taxol of the present invention was based on 159 patients randomized into the four treatment Arms previously described. Of the 159 patients, 157 patients received at least one dose of taxol and were evaluated for both safety and efficacy.

528 courses of taxol were given to 157 patients distributed over the 4 treatment Arms. The median number of courses received was 3 (range 1–8), which is equivalent to a median of 9 weeks of study. Overall 27 of 157 (17%) patients required a dose reduction, mainly for neutropenia with less than 500 cells/cmm for more than 7 day duration. Taxol administration was discontinued for 2 patients during the second course. One of the 27 patients was retreated at a reduced dose level, and dosage was re-escalated after one course at a reduced dose level. Overall, 11% of the taxol courses were administered at reduced dosage.

Dose reduction was required in the 2 Arms using long term infusion more frequently than in Arms using the short term infusion. This is surprising considering that a more concentrated dosage of taxol is given during the short infusion than during the long infusion.

The time between courses ranged from 17 to 49 days, with the median number of days between courses being 21. the following table lists the various premedications used in the various treatment Arms

TABLE 1

EXAMPLES OF PREMEDICATIONS USED

| H-2 Receptor Blocker: | Steroid: | Antihistimine: |
|---|---|---|
| Ranitidine | Dexamethasone | Dyphenhydramine |
| Famotidine | Hydrocortisone | Clemastine |
| Cimetidine | Prednisone | Chlorpheniramine |
|  |  | Chlorphenamine |
|  |  | Dimethindene maleate |
|  |  | Promethazine |

In a preferred embodiment, at least one of each of the H-2 receptor blockers, steroids and antihistimines is utilized. By way of non-limiting examples, a combination of prednisone and hydrocortisone, or dexamethasone and hydrocortisone could be used in combination with at least one of the antihistamines and least one of the H-2 receptor blockers.

22 patients achieved an objective response (CR or PR). Thus, the overall objective response rate is 14% (22/157) for this study. However, 17 patients were not evaluated and another five patients were unevaluable. If these latter patients are excluded, the objective response rate is 16% (22/135). Further, 51 patients with stable disease were continued on taxol and may later meet the criteria for an objective response (Note that an average of only three courses of taxol yielded the present results). Thus, use of the present method for administration of taxol produces at least a 14% overall objective response rate for 157 patients. This is an astonishing result, since all of the patients were considered drug refractory. It is also remarkable that 3 out of 46 (7%) of these patients who had progressed on previous platinum containing chemotherapy responded to taxol. Overall, response to taxol occurred in 13% of patients (14/114) who were considered resistant to platinum therapy (i.e., progression on therapy or relapse within six months). Further, 52% of patients (24/46) with disease truly refractory to platinum, and 53% of patients (16–36) with an early relapse after platinum, achieved a stabilization of their disease.

15% of the platinum resistant patients who had received one previous regimen of platinum responded to taxol, versus 10% of the platinum resistant patients who had received two previous regimens of platinum, corresponding to 19 and 23%, respectively.

Of 159 patients, only one died of taxol related toxicity (less than 1%).

HEMATOLOGIC TOXICITY

Another aspect of the present invention is the reduction in hematologic toxicity associated with the treatment of cancer with taxol. The 157 patients who received taxol had blood counts performed weekly. White blood cell (WBC) counts, absolute neutrophil count (ANC), platelet counts, and hemoglobin (Hb) concentration were the primary variables used to evaluate treatment related myelosuppression. The World Health Orgination, WHO, grades of nadir for the entire study population of 157 patients during course 1 are presented in the table below. Leukopenia and neutropenia were the most frequent and severe hematologic adverse effects observed during the first couse of treatment. 53% (83/156) of the patients had Grade III or IV neutropenia, while 39% (61/157) had Grade III or IV leukopenia. Severe thrombocytopenia was observed in only two patients (1%) during course 1.

Of particular significance is that Grade IV neutropenia was reported almost five times more frequently in the patients treated with the 24-hour taxol infusion than the patients treated with a 3-hour taxol infusion.

TABLE 2

Myelotoxicity Course 1 WBC Grade For Treatment Arm

|  | 175/4 (n = 45) n (%) | 175/3 (n = 29) n (%) | 135/24 (n = 44) n (%) | 135/3 (n = 39) n (%) | TOTAL (n = 157) n (%) |
|---|---|---|---|---|---|
| WBC Count |  |  |  |  |  |
| 0 | 1 (2) | 11 (38) | 4 (9) | 15 (38) | 31 (20) |
| I | 5 (11) | 6 (21) | 5 (11) | 13 (33) | 29 (18) |
| II | 11 (25) | 7 (24) | 11 (25) | 7 (18) | 36 (23) |
| III | 22 (49) | 5 (17) | 20 (46) | 3 (8) | 50 (32) |
| IV | 6 (13) | 0 — | 4 (9) | 1(3) | 11 (7) |
| AMC Count |  |  |  |  |  |
| 0 | 2 (5) | 11 (38) | 6 (14) | 18 (46) | 37 (24) |
| I | 1 (2) | 2 (7) | 2 (15) | 8 (21) | 13 (8) |
| II | 5 (11) | 3 (10) | 7 (16) | 8 (21) | 23 (15) |
| III | 8 (18) | 6 (21) | 6 (14) | 4 (10) | 24 (15) |
| IV | 28 (63) | 7 (24) | 23 (52) | 1 (3) | 59 (38) |
| Platelet Count |  |  |  |  |  |
| 0 | 39 (87) | 29 (100) | 43 (98) | 36 (92) | 147 (94) |
| I | 3 (7) | 0 | 1 (2) | 2 (5) | 6 (4) |
| II | 1 (2) | 0 | 0 | 1 (3) | 2 (1) |
| III | 1 (2) | 0 | 0 | 0 | 1 (1) |
| IV | 1 (2) | 0 | 0 | 0 | 1 (1) |

As is clear from Table 2, grade 4 neutropenia was reported almost 5 times more frequently in patients treated with the 24-hour taxol infusion compared to patients treated by a 3-hour infusion. 58% (51/88) of the patients treated with the 24-hour taxol infusion had grade 4 neutropenia in comparison to 12% (8/68) of the patients treated by a 3-hour infusion. When the incidence of grade 3 and grade 4 are pooled, it is clear that severe leukopenia occurs more frequently in patients treated with a 24-hour taxol infusion than with a 3-hour infusion.

With reference to Table 3 below, analysis of median values for nadir count confirms the severity of taxol induced neutropenia, especially in the two 24-hour treatment Arms.

TABLE 3

Myelotoxicity Course 1 = Nadir Counts, Pre Treatment Arm

|  | 175/4 (n = 45) | 175/3 (n = 29) | 135/24 (n = 44) | 135/3 (n = 39) | TOTAL (n = 157) |
|---|---|---|---|---|---|
| WBC Count[1] |  |  |  |  |  |
| Median | 1,600 | 3,300 | 1,900 | 3,700 | 2,400 |
| Range | 300–7,300 | 1,400–13,900 | 500–7,800 | 980–6,850 | 300–13,900 |

TABLE 3-continued

Myelotoxicity Course 1 = Nadir Counts, Pre Treatment Arm

|  | 175/4 (n = 45) | 175/3 (n = 29) | 135/24 (n = 44) | 135/3 (n = 39) | TOTAL (n = 157) |
|---|---|---|---|---|---|
| AMC Count | | | | | |
| Median | 330 | 1,390 | 470 | 1,930 | 840 |
| Range | 0–664 | 210–11,770 | 0–555 | 360–6,290 | 0–11,770 |
| Platelet Count | | | | | |
| Median | 168,000 | 285,000 | 236,500 | 298,000 | 226,000 |
| Range | 11,000–345,000 | 144,000–688,000 | 87,000–710,000 | 65,000–749,000 | 11,000–749,000 |

$^{(1)}$Cell counts expressed in number of cells/cm.

Further, anemia of any grade occurred in 47% (26/55) of patients with normal baseline Hb values who had been treated with a taxol long-term infusion, and anemia occurred in only 28% of patients treated with the short-term infusion. In summary, neutropenia and leukopenia were the most frequent and severe hematologic adverse effects during the study period, with 63% of the patients displaying severe neutropenia (WHO Grade III and IV) during at least one couse. The incidence of severe neutropenia in the long-term infusion versus the short-term infusion Arms was 85% versus 32%. The incidents of severe neutropenia in the high dose Arms was 74% (55/74) versus 52% (43/83) in the low dose Arms. Thus, it is clear that both reducing the dosage and the infusion time will lower hematologic toxicity; however, reducing the infusion to 3 hours from 24 hours appears to have a greater impact on reducing toxicity than reducing the taxol dosage from about 175 mg/m$^2$ to 135 mg/m$^2$.

Those patients suffering from myelotoxicity can be treated with colony stimulating factors, CSFs. In a preferred embodiment, patients are given granulocyte colony stimulating factors in an amount sufficient to be effective in either reducing myelotoxicity or increasing the rate of recovery from myelotoxicity. Preferably, the CSFs are provided in accordance with the method taught by Sarosy et al. in "Phase I Study of Taxol and Granulocyte Colony-Stimulating Factor In Patients With Refractory Ovarian Cancer," *Journal of Clincal Oncology*, Vol. 10, No. 7, (July, 1982) pp. 1165–1170. In a preferred embodiment, G-CSF (available from Amgen, Inc. of Thousand Oaks, Calif.) can be self-administered subcutaniously on a daily basis (thus allowing for treatment on an outpatient basis), with injections beginning 24 hours after the completion of a taxol infusion. Preferably a G-CSF dose of about 10 µg/kg/d is used, and G-CSF injection continues until there is convincing evidence of bone marrow recovery from taxol-induced nadir. Convincing evidence of bone marrow recovery includes a white blood cell count of 10,000 cells/mm$^2$ and a platelet count of more than 50,000/mm$^2$. The use of G-CSF enables higher doses of taxol to be used, and allows for certain patients suffering severe milosuppression to be continued on taxol treatment whereas, in the past, such patients may not have been allowed to continue on taxol.

HYPERSENSITIVITY REACTIONS

35% (57/157) of the patients exhibited some type of hypersensitivity reaction. Only two hypersensitivity reactions (2 of 157 patients or 1%) were reported which required acute therapeutic intervention.

Table 4 below lists the number and percentage of patients demonstrating hypersensitivity reactions per treatment Arm and also provides the type of HSR per course.

TABLE 4

Hypersensitivity Reactions (MSR) Per Treatment Arm

|  | 175/4 n (%) | 175/3 n (%) | 135/24 n (%) | 135/3 n (%) | TOTAL n (%) |
|---|---|---|---|---|---|
| Per Patient | | | | | |
| Number of patients analyzed | 45 | 29 | 44 | 39 | 157 |
| Patients reporting a HSR Per Course | 6 (36) | 12 (41) | 18 (41) | 11 (28) | 57 (36) |
| Number of courses analyzed | 163 | 92 | 141 | 132 | 528 |
| Courses with a reported HSR | 46 (28) | 23 (25) | 44 (31) | 23 (17) | 136 (26) |
| Type of HSR Per Course$^{(1)}$ | | | | | |
| Flushing | 32 | 16 | 40 | 15 | 103 |
| Rash | 3 | 6 | 6 | 6 | 21 |
| Hypotension | 10 | 1 | 1 | 1 | 13 |
| Dyspriea | — | — | 3 | 2 | 5 |
| Ederma face | 1 | 1 | — | — | 2 |
| Eye disorder | — | — | — | 2 | 2 |
| Pruritis | — | — | — | 2 | 2 |
| Headache | — | — | 1 | — | 1 |
| Arrhytheria | 1 | — | — | — | 1 |
| Hypertension | 1 | — | — | — | 1 |
| Tachychardia | — | — | 1 | — | 1 |
| Nausea/Vomiting | — | — | 1 | — | 1 |
| Chest pain | — | — | 1 | — | 1 |

$^{(1)}$More than 1 sign and symptom may be experienced in each course.

The most frequent symptoms were flushing, mainly confined to the face, following by skin rash, hypotension, and dyspnea.

Of the two patients suffering severe hypersensitivity reactions, one patient was not rechallenged with taxol. The other patients suffering a severe hypersensitivity reaction received a 135 mg/mm$^2$ 24-hour infusion first course of taxol without experiencing a severe hypersensitivity reaction. Due to WHO Grade IV neutropenia for more than 7 days, the scheduled dose for course 2 was reduced by 20%. During the second course, the delivery of less than 1 ml of taxol infusion induced tachychardia and shortness of breath, requiring the infusion to be stopped. The patient developed an extreme general flush, with a heart rate of 150 per minute (regular) and the blood pressure was 150/100. The allergic reaction resolved completely after the administration of 50 mg benadryl IV and 35 mg adrenalin s.c. The infusion of taxol was restarted after and interruption of 70 minutes at the regular infusion rate without further problems.

Another patient encountered a hypersensitivity reaction, which prompted the investigator to interrupt the infusion. However, this incident did not qualify as a significant HSR. During a first course, the patient received 135 mg/m$^2$ during a 24-hour infusion. Course 1 was administered uneventfully. Taxol infusion during course 2 was interrupted after 1 minute (less than 1 mg of taxol) due to dyspnea, flushing, and nausea, which was treated with 5 mg of chlorphenamine. The patient received another 250 mg hydrocortisone, and the taxol infusion was recommenced 70 minutes after. The total infusion time was 28 hours, 15 minutes with no further occurrence of hypersensitivity reaction. Course 3 was administered uneventfully with normal premedication.

Further examples of adverse reactions are discussed later.
PERIPHERAL NEUROPATHY 80 of 157 patients (51%) experienced some sign of symptom of peripheral neurotoxicity. The incidents in the high dose arms was 66% (49/74), while the incidents in the low dose arms was 37% (31/83). The incidents of peripheral neuropathy in the long-term (24-hour) infusion was 48% (43/89), while the incidents of peripheral neuropathy in the short-term infusion arms was 50% (37/68).

Prior to taxol treatment, 75% (118/157) of patients were asymptomatic; of these, 44 patients (37%) developed some peripheral neuropathy symptoms. Overall, 54 to 157 patients (34%) developed, or had worse peripheral neuropathy symptoms, as can be seen by Table 5 below.

The substantial reduction in peripheral neurotoxicity symptoms (PNS) in patients receiving lower dosage of taxol allows for more flexibility in treating patients, since lower taxol dosages over longer infusion periods can be used for patients suffering from PNS while higher doses and/or shorter infusion periods can be used for patients not suffering from PNS.

TABLE 5

Peripheral Neuropathy Symptoms (PNS) and Taxol Dosing
By Treatment Arm

|  | 175/4 n = 45 n (%) | 175/3 n = 29 n (%) | 135/24 n = 44 n (%) | 135/3 n = 39 n (%) | TOTAL n = 157 n (%) |
|---|---|---|---|---|---|
| Number of Patients Who Developed or Worsened PNS | 20 (44) | 18 (62) | 7 (16) | 8 (21) | 54 (34) |
| First Occurence/ Worsening of PNS By Courses |  |  |  |  |  |
| Course 1 | 9 | 7 | 3 | 4 | 23/157 (15) |
| Course 2 | 8 | 9 | 2 | — | 19/143 (13) |
| Course 3 | 1 | 1 | 1 | 1 | 4/95 (4) |
| Course 4 and more | 2 | 1 | 1 | 3 | 7/69 (10) |
| By Cumulative Dose of Taxol |  |  |  |  |  |
| ≦200 mg/m$^2$ | 9 | 7 | 3 | 4 | 23 |
| 201–400 mg/m$^2$ | 8 | 9 | 3 | 1 | 22 |
| 401–600 mg/m$^2$ | 2 | 1 | 1 | 2 | 4 |
| >600 mg/m$^2$ | 1 | 1 | 1 | 2 | 5 |

It is clear that peripheral neuropathy symptoms (PNS) are reduced when a dosage of about 135 mg/m$^2$ taxol is provided rather than a dosage of about 175 mg/m$^2$.

Further examples of adverse drug reactions, and the procedures used to continue treatment follow.

Patient BB-2 was allocated to the 135 mg/m$^2$, 3 hour arm. Shortly after beginning her second cycle of treatment, she developed asymptomatic bradyarrhythmia characterized by short periods of AV block or sinus pauses accompanied by some ventricular extrasystoles. She had some extrasystols in cycle 1 as well. There was no prior cardiac history and subsequent investigations were normal. She had pacemaker inserted and was retreated with a third cycle. The bradyarrhythmia appeared to have a definite relation to taxol, and the patient recovered with treatment.

Patient BB-3 was allocated to the a175 mg/m$^2$, 3 hour arm. Shortly after beginning cycle 2, she developed a hypersensitivity reaction, characterized by generalized urticaria, diaphoresis, and dyspena. The infusion was interrupted and she recovered quickly after treatment with epinephrine and antihistamine. She was retreated using the re-challenge amendment discussed above. The HSR appeared to be definitely related to taxol, and the patient recovered with treatment.

Patient DF-1 was randomized to the 135 mg/m$^2$, 24 hour arm. During her first treatment, she had 2 episodes of asymptomatic bradycardia, during which the infusion was interrupted for durations lasting 3 and 5 minutes, respectively. She also developed a mild skin rash. However, the infusion was completed. The bradycardia appeared related to taxol, and the patient recovered.

Patient IM-7 was allocated to the 135 mg/m$^2$, 24 hour infusion, and experienced a non-significant HSR during cycle 2. Her first cycle of treatment has been uneventful; however, 5 minutes after the 2nd treatment began, she became flushed and dyspneic, with nausea (no vomiting). The infusion was stopped, 5 mg chlorpheniramine was given and symptoms rapidly resolved. The patient was re-treated according to the retreatment protocol discussed earlier with no problem, aside from minor facial rash. The HSR appeared to be related to taxol.

Patient-MP-7 was allocated to the 135 mg/m$^2$, 24 hour infusion. About 30 minutes after cycle 1 began, she became hot, flushed, and slightly dyspneic (BP 114/80, pulse 112). Taxol was stopped, she was given diphenhydramine, and the reaction resolved immediately. The patient was re-treated according to the re-treatment protocol without event. Thus, the HSR appears related to taxol.

Patient-VA-30 was randomized to the 135 mg/m$^2$, 24 hour arm. During her second treatment, she developed flushing and a sense of tightness in her throat. The infusion was stopped for a short while, and repeat doses of steroid, antihistamine was ranitidine were given. Taxol was restarted with no further problems; this indicates that the HSR was caused by taxol.

The success of the use of the new taxol infusion protocol of the present invention in the treatment of ovarian cancer makes it readily apparent that anti-neoplastically effective dosages of taxol can be infused over much shorter time periods than was previously believed possible, without inducing severe hypersensitivity reactions or inducing fatal anaphylactic shock. Thus, it is contemplated that the infusion protocol of the present invention may be utilized to treat solid tumors and leukemias, such as but not limited to lung cancer, breast cancers, and ovarian cancers. It is to be understood that treatment of different forms of cancer may require the adjustment of the taxol dosage to have optimal efficacy.

The foregoing clearly establishes that taxol is both safe and effective in the treatment of cancer, such as ovarian cancer, when administered according to the protocol of the present invention. In particular, by use of a 3-hour infusion of about 135 mg/m$^2$ taxol, following premedication, a substantial reduction results in the frequency of myelotoxicity and neuropathy associated with the administration of taxol to patients suffering from cancer. Further, patients who exhibit severe hypersensitivity reactions can be rechallenged with taxol after treating the HSR symptoms by use of an infusion of about 24 hours or greater, preferably using a dosage of about 135 mg/m$^2$ to about 175 mg/m$^2$. Preferably, colony stimulation factors are administered to assist in ameliorating myelosuppression.

The use of lower dosages of taxol to achieve antineoplastic results will allow for more patients to be treated with the present limited supply of taxol. Further, depending upon the toxicities noted in a patient during treatment with taxol according to the present protocol, the duration of infusion can be extended or shortened, or the taxol dosage can be reduced or increased, thus providing more flexibility in treating cancer with taxol. Further, patients capable of handling higher doses of taxol can be administered up to about 275 mg/m$^2$; should the patient encounter severe toxicity, such as a severe neuropathy, the protocol of the present invention allows for reducing the dosage.

From the above teachings, it is readily apparent that many modifications and variations of the present invention are possible. It is to be therefore understood that the invention may be practiced than as otherwise specifically described.

We claim:

1. A method for treating a patient suffering from a taxol-sensitive tumor to effect regression of said tumor while effecting reduced hematologic toxicity and comprising:

a. premedicating said patient with a medicament that reduces or eliminates hypersensitivity reactions said premedicating comprising (a1) orally administering an effective amount of dexamethasone approximately 12 and 6 hours prior to parenterally administering taxol; and (a2) after administering said dexamethasone, intravenously administering (i) an effective amount of an antihistamine and (ii) an effective amount of cimetidine or ranitidine, prior to parentally administering taxol; and b. parenterally administering to said patient about 175 mg/m$^2$ taxol over a duration of about 3 hours.

2. The method of claim 1, further comprising repeating said method at an interval of about 3 weeks.

3. The method of claim 2, wherein said method is repeated for at least two cycles and further comprising evaluating a response in said patient after every two cycles.

4. The method of claim 3, comprising repeating the method upon evaluation of a complete response or partial response in said patient.

5. The method of claim 1, wherein said premedicating comprises (a1) orally administering 20 mg of dexamethasone approximately 12 and 6 hours prior to parentally administering taxol; and (a2) after administering said dexamethasone, intravenously administering (i) 50 mg of an antihistamine and (ii) 50 mg of ranitidine, prior to parentally administering taxol.

6. A method for treating a patient suffering from a taxol-sensitive ovarian tumor to effect regression of said tumor while effecting reduced hematologic toxicity and comprising:

a. premedicating said patient with a medicament that reduces or eliminates hypersensitivity reactions said premedicating comprising (a1) orally administering an effective amount of dexamethasone approximately 12 and 6 hours prior to parentally administering taxol; and (a2) after administering said dexamethasone, intravenously administering (i) an effective amount of an antihistamine and (ii) an effective amount of cimetidine or ranitidine, prior to parentally administering taxol; and b. parenterally administering to said patient about 135 or about 175 mg/m$^2$ taxol over a duration of about 3 hours.

7. The method of claim 6, further comprising repeating said method at an interval of about 3 weeks.

8. The method of claim 7, wherein said method is repeated for at least two cycles and further comprising evaluating a response in said patient after every two cycles.

9. The method of claim 8, comprising repeating the method upon evaluation of a complete response or partial response in said patient.

10. The method of claim 6, wherein said patient has previously been treated with chemotherapy for ovarian cancer.

11. The method of claim 6, wherein said premedicating comprises (a1) orally administering 20 mg of dexamethasone approximately 12 and 6 hours prior to parentally administering taxol; and (a2) after administering said dexamethasone, intravenously administering (i) 50 mg of an antihistamine and (ii) 50 mg of ranitidine, prior to parentally administering taxol.

* * * * *

Disclaimer 6,414,014—Renzo Mauro Canetta, Madison, CT; Elezabeth Eisenhauer, Kinston, CA; Marcel Rozencweig, Brandford, CT. METHOD FOR ADMINISTRATION OF TAXOL. Patent dated July 2, 2002. Disclaimer filed July 16, 2002 by the assignee, Bristol-Myers Squibb Company.

Hereby disclaims and dedicates to the Public all claims and entire term of said patent.
*(Official Gazette, September 10, 2002)*